United States Patent
Arnold et al.

(10) Patent No.: US 11,024,024 B2
(45) Date of Patent: Jun. 1, 2021

(54) SYSTEMS AND METHODS FOR ANALYZING PERFUSION-WEIGHTED MEDICAL IMAGING USING DEEP NEURAL NETWORKS

(71) Applicant: The Regents of the University of California, Oakland, CA (US)

(72) Inventors: Corey Arnold, Oakland, CA (US); King Chung Ho, Oakland, CA (US); Fabien Scalzo, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 304 days.

(21) Appl. No.: 16/062,159

(22) PCT Filed: Dec. 15, 2016

(86) PCT No.: PCT/US2016/066877
§ 371 (c)(1),
(2) Date: Jun. 14, 2018

(87) PCT Pub. No.: WO2017/106469
PCT Pub. Date: Jun. 22, 2017

(65) Prior Publication Data
US 2018/0374213 A1 Dec. 27, 2018

Related U.S. Application Data

(60) Provisional application No. 62/267,328, filed on Dec. 15, 2015.

(51) Int. Cl.
*G06T 7/00* (2017.01)
*G06N 3/04* (2006.01)
(Continued)

(52) U.S. Cl.
CPC .......... *G06T 7/0012* (2013.01); *A61B 5/0263* (2013.01); *G06N 3/049* (2013.01);
(Continued)

(58) Field of Classification Search
None
See application file for complete search history.

(56) References Cited

U.S. PATENT DOCUMENTS 7,693,349 B2 4/2010 Gering
8,873,813 B2 10/2014 Tadayon
(Continued)

OTHER PUBLICATIONS

An, H., et al., "Defining the Ischemic Penumbra Using Magnetic Resonance Oxygen Metabolic Index," Stroke, vol. 46, No. 4, pp. 982-988, 2015.
(Continued)

*Primary Examiner* — Tahmina N Ansari
(74) *Attorney, Agent, or Firm* — Quarles & Brady LLP

(57) ABSTRACT

Systems and methods for analyzing perfusion-weighted medical imaging using deep neural networks are provided. In some aspects, a method includes receiving perfusion-weighted imaging data acquired from a subject using a magnetic resonance ("MR") imaging system and modeling at least one voxel associated with the perfusion-weighted imaging data using a four-dimensional ("4D") convolutional neural network. The method also includes extracting spatio-temporal features for each modeled voxel and estimating at least one perfusion parameter for each modeled voxel based on the extracted spatio-temporal features. The method further includes generating a report using the at least one perfusion parameter indicating perfusion in the subject.

23 Claims, 7 Drawing Sheets

(51) Int. Cl.
 *A61B 5/026* (2006.01)
 *G06N 5/04* (2006.01)
(52) U.S. Cl.
 CPC ......... *G06N 5/046* (2013.01); *G06K 2209/05* (2013.01); *G06T 2200/04* (2013.01); *G06T 2207/10096* (2013.01); *G06T 2207/20081* (2013.01); *G06T 2207/20084* (2013.01); *G06T 2207/30016* (2013.01); *G06T 2207/30096* (2013.01); *G06T 2207/30104* (2013.01)

(56) References Cited

U.S. PATENT DOCUMENTS

| | | | | |
|---|---|---|---|---|
| 10,438,347 | B2* | 10/2019 | Enzmann | G06T 7/0012 |
| 2004/0127799 | A1 | 7/2004 | Sorenson | |
| 2013/0338489 | A1* | 12/2013 | Prisk | A61B 5/055 600/420 |
| 2015/0112182 | A1* | 4/2015 | Sharma | A61B 5/7282 600/408 |
| 2015/0141804 | A1* | 5/2015 | Rooney | A61B 5/0295 600/419 |
| 2018/0374213 | A1* | 12/2018 | Arnold | A61B 5/0263 |

OTHER PUBLICATIONS

Bergstra J., et al., "Random Search for Hyper-Parameter Optimization," J. of Machine Learn. Res., vol. 13, pp. 281-305, 2012.
Calamante, F., et al., "The physiological significance of the time-to-maximum (Tmax) parameter in perfusion MRI," Stroke, vol. 41, No. 6, pp. 1169-1174, 2010.
Chen, B., et al, "Deep Learning of Invariant Spatio—Temporal Features from Video," NIPS Work., no. Aug. pp. 1-9, 2010.
Christensen, et al., "Comparison of 10 Perfusion MRI Parameters in 97 Sub-6-Hour Stroke Patients Using VoxelBased Receiver Operating Characteristics Analysis," Stroke, vol. 40, pp. 2055-2061, 2009.
Ford, A.L. et al, "Clinically Relevant Reperfusion in Acute Ischemic Stroke: MTT Performs Better than Tmax and TTP," Transl. Stroke Res., vol. 5, No. 3, pp. 415-421, 2014.
Furlan, A.J. "Endovascular Therapy for Stroke—It's about Time," N. Engl. J. Med., pp. 1-3, 2015.
Glorot, X., et al., "Deep Sparse Rectifier Neural Networks," Proc. 14th Int. Cont. Artif. Intel/. Statistics 2011, vol. 15, pp. 315-323, 2011.
Goyal, M., et al., "Perfusion imaging in acute ischemic stroke: let us improve the science before changing clinical practice.," Radiology, vol. 266, No. 1, pp. 16-21, 2013.
Grotta J.C., et al, "Stroke Neurologist's Perspective on the New Endovascular Trials," Stroke, vol. 46, No. 6, pp. 1447-1452, 2015.
Hyvarinen, A. et al., Natural image statistics: A probabilistic Approach to Early Computational Vision. Springer Science & Business Media, 2009. (two parts due to file size).
International Search Report and Written Opinon for PCT/US2016/066877, dated Feb. 24, 2017, 12 pages.
Kane, I., et al. "Comparison of 10 different magnetic resonance perfusion imaging processing methods in acute ischemic stroke: Effect on lesion size, proportion of patients with diffusion/perfusion mismatch, clinical scores, and radiologic outcomes," Stroke, vol. 38, No. 12, pp. 3158-3164, 2007.
Krizhevsky, A., et al., "ImageNet Classification with Deep Convolutional Neural Networks," Adv. Neural Inf. Process. Syst., pp. 1-9, 2012.
Lai, V., "Application of Diffusion- and Perfusion—Weighted Imaging in Acute Ischemic Stroke." vol. 25, No. 2010, 2014.
Le, Q. V., et al. "Learning hierarchical invariant spatio-temporal features for action recognition with independent subspace analysis," Proc. IEEE Comput. Soc. Cont Comput. Vis. Pattern Recognit., pp. 3361-3368, 2011.
Le, Q. V., et al. "Tiled convolutional neural networks." Advances in neural information processing systems. 2010.
Legrand, L., et al., "Do FLAIR Vascular Hyperintensities beyond the DWI Lesion Represent the Ischemic Penumbra?," AJNR. Am. J. Neuroradiol., vol. 36, No. 2, pp. 269-274, 2015.
Majoie C. B. L. M., et al. "Intraarterial Treatment for Acute Ischemic Stroke," N. Engl. J. Med., vol. 372, No. 12, pp. 1176-1179, 2015.
Menon, B.K., et al., "Role of Imaging in Current Acute Ischemic Stroke Workflow for Endovascular Therapy," Stroke, vol. 46, No. 6, pp. 1453-1461, 2015.
Mobahi, H., et al. "Deep Learning from Temporal Coherence in Video," Proc. 26th Annu. Int. Cont Mach. Learn., pp. 737-744, 2009.
Nair V., et al., "Rectified Linear Units Improve Restricted Boltzmann Machines," Proc. 27th Int. Cont. Mach. Learn., No. 3, pp. 807-814, 2010.
Olivot, J.M., et al, "Optimal tmax threshold for predicting penumbra! tissue in acute stroke," Stroke, vol. 40, No. 2, pp. 469-475, 2009.
Russakovsky, O., et al., "ImageNet Large Scale Visual Recognition Challenge," Arxiv, p. 37, 2014.
Taylor, G. W., et al. "Convolutional learning of spatio-temporal features," in Computer Vision—ECCV, 2010, pp. 140-153.

\* cited by examiner

SYSTEMS AND METHODS FOR ANALYZING PERFUSION-WEIGHTED MEDICAL IMAGING USING DEEP NEURAL NETWORKS

CROSS-REFERENCE TO RELATED APPLICATIONS

This application represents the national stage entry of International Application PCT/US2016/066877 filed Dec. 15, 2016, which claims benefit of U.S. Provisional Application 62/267,328 filed Dec. 15, 2015, which is incorporated herein by reference in its entirety for all purposes.

STATEMENT REGARDING FEDERALLY SPONSORED RESEARCH

This invention was made with government support under NS076534, awarded by the National Institutes of Health. The government has certain rights in the invention.

BACKGROUND

The field of the invention is directed to magnetic resonance ("MR") imaging. More particularly, the present disclosure is directed to systems and methods for performing and analyzing perfusion-weighted medical imaging.

Any nucleus that possesses a magnetic moment attempts to align itself with the direction of the magnetic field in which it is located. In doing so, however, the nucleus precesses around this direction at a characteristic angular frequency (Larmor frequency), which is dependent on the strength of the magnetic field and on the properties of the specific nuclear species (the magnetogyric constant γ of the nucleus). Nuclei which exhibit these phenomena are referred to herein as "spins."

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. A net magnetic moment $M_z$ is produced in the direction of the polarizing field, but the randomly oriented magnetic components in the perpendicular, or transverse, plane (x-y plane) cancel one another. If, however, the substance, or tissue, is subjected to a transient electromagnetic pulse (excitation field $B_1$) which is in the x-y plane and which is near the Larmor frequency, the net aligned moment, $M_z$, may be rotated, or "tipped", into the x-y plane to produce a net transverse magnetic moment Mt, which is rotating, or spinning, in the x-y plane at the Larmor frequency. The practical value of this phenomenon resides on signals that are emitted by the excited spins after the pulsed excitation signal $B_1$ is terminated. Depending upon chemically and biologically determined variable parameters such as proton density, longitudinal relaxation time ("T1") describing the recovery of $M_z$ along the polarizing field, and transverse relaxation time ("T2") describing the decay of $M_t$ in the x-y plane, this nuclear magnetic resonance ("NMR") phenomena is exploited to obtain image contrast and concentrations of chemical entities or metabolites using different measurement sequences and by changing imaging parameters.

When utilizing NMR to produce images and chemical spectra, a technique is employed to obtain NMR signals from specific locations in the subject. Typically, the region to be imaged (region of interest) is scanned using a sequence of NMR measurement cycles that vary according to the particular localization method being used. To perform such a scan, it is, of course, necessary to elicit NMR signals from specific locations in the subject. This is accomplished by employing magnetic fields ($G_x$, $G_y$, and $G_z$) which have the same direction as the polarizing field $B_0$, but which have a gradient along the respective x, y and z axes. By controlling the strength of these gradients during each NMR cycle, the spatial distribution of spin excitation can be controlled and the location of the resulting NMR signals can be identified from the Larmor frequencies typical of the local field. The acquisition of the NMR signals is referred to as sampling k-space, and a scan is completed when sufficient NMR cycles are performed to fully or partially sample k-space. The resulting set of received NMR signals are digitized and processed to reconstruct the image using various reconstruction techniques.

To generate an MR anatomic image, gradient pulses are typically applied along the x, y and z-axis directions to localize the spins along the three spatial dimensions, and MR signals are acquired in the presence of one or more readout gradient pulses. An image depicting the spatial distribution of a particular nucleus in a region of interest of the object is then generated, using various post-processing techniques. Typically, the hydrogen nucleus (1H) is imaged, though other MR-detectable nuclei may also be used to generate images.

Perfusion-weighted MRI is a common imaging technique that is used in the clinical treatment of patients with brain pathologies, such as stroke or cancer. Perfusion-weighted images ("PWI") are typically obtained by injecting a contrast bolus, such as a gadolinium chelate, into a patient's bloodstream and imaging as the bolus passes through the patient using dynamic susceptibility contrast ("DSC") or dynamic contrast enhanced ("DCE") imaging techniques. The susceptibility effect of the paramagnetic contrast leads to signal loss that can be used to track contrast concentration in specific tissues over time. By applying various models to the resulting concentration-time curves, a number of perfusion parameters can be determined, such as blood volume ("BV"), blood flow ("BF"), mean transit time ("MTT"), time-to-peak ("TTP"), time-to-maximum ("$T_{max}$"), maximum signal reduction ("MSR"), first moment ("FM"), and others.

Previously, PWI have been analyzed by using deconvolution methods. In these approaches, the measured concentration of contrast in each voxel as a function of time is expressed as the convolution between an arterial input/venous output concentration and a residual curve, which expresses the residual amount of contrast in each voxel. By applying various deconvolution algorithms, such as algorithms based on single value decomposition ("SVD"), different perfusion parameters may be obtained and used to determine a chronic or acute condition of the patient. For example, $T_{max}$ and MTT have been used to predict a risk of infarction.

However, there are growing concerns that perfusion parameters obtained using deconvolution techniques are less predictive due to errors and distortions introduced during the deconvolution process. In addition, values for the generated parameters and hence conclusions drawn thereupon can vary depending upon the specific models and model assumptions utilized. For example, the infarct core and penumbra regions or their ratio, computed using TTP or $T_{max}$, have been used to guide treatment decisions in acute stroke patients. However, the appropriate thresholds for TTP or $T_{max}$ identifying core and penumbra regions are still subject to debate.

In light of the above, there is a need for improved image analysis techniques that can provide accurate information for the diagnosis and treatment of patients, such as information regarding the irreversibly infarcted tissue or abnormal tissue.

SUMMARY

The present disclosure overcomes the drawbacks of previous technologies by providing systems and methods for analyzing perfusion-weighted medical imaging using a neural network architecture. In particular, a convolutional neural network ("CNN") architecture may be used. Aspects of this technology include building and applying deep CNNs with four-dimensional ("4D") convolutions to extract imaging features from perfusion-weighted medical imaging. The imaging features can be used to generate information useful in diagnosis and treatment of various patient conditions.

In accordance with one aspect of the disclosure, a method for analyzing perfusion-weighted medical imaging using deep neural networks is provided. The method includes receiving perfusion-weighted imaging data acquired from a subject using a magnetic resonance ("MR") imaging system and modeling at least one voxel associated with the perfusion-weighted imaging data using a four-dimensional ("4D") convolutional neural network. The method also includes extracting spatio-temporal features for each modeled voxel and estimating at least one perfusion parameter for each modeled voxel based on the extracted spatio-temporal features. The method further includes generating a report using the at least one perfusion parameter indicating perfusion in the subject.

In accordance with another aspect of the disclosure, a system for analyzing perfusion-weighted imaging. The system includes an input configured to receive perfusion-weighted imaging data acquired from a subject using a magnetic resonance ("MR") imaging system and a processor programmed to execute instructions stored in a non-transitory computer readable media to access the perfusion-weighted imaging data. The processor is also programmed to generate an input patch for each selected voxel associated with the perfusion-weighed imaging data, and apply a four-dimensional ("4D") convolutional neural network to the generated input patch to extract spatio-temporal features. The processor is further programmed to compute at least one perfusion parameter using the spatio-temporal features extracted, and generate a report using the at least one perfusion parameter. The system further include an output for displaying the report to communicate perfusion in the subject.

The foregoing and other aspects and advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

The present invention will hereafter be described with reference to the accompanying drawings, wherein like reference numerals denote like elements. The patent or application file contains at least one drawing executed in color. Copies of this patent or patent application publication with color drawing(s) will be provided by the Office upon request and payment of the necessary fee.

DETAILED DESCRIPTION

The present disclosure is directed to systems and methods for analyzing temporal medical imaging data, and more specifically perfusion-weighted medical imaging data. Current techniques apply singular value decomposition algorithms to deconvolve image signals to obtain perfusion parameters, such as time-to-maximum ("$T_{max}$"). These parameters are then used to characterize tissue properties, and predict tissue and patient outcomes. However, studies have found that the deconvolution process can introduce distortions that influence the measurement of perfusion parameters, such as $T_{max}$, and the decoupling of delay may negatively impact prediction. In addition, perfusion parameters can vary when different computational methods are used, leading to an inconsistency in prediction.

To address the drawbacks of current approaches, the present disclosure introduces a generalized deep convolutional neural network ("CNN") architecture that can estimate perfusion parameters, as well as automatically learn hierarchical spatio-temporal features. These features allow for a more precise quantification of perfusion-weighed imaging, and can support a variety of biomedical applications, including predicting tissue death (infarction) at the voxel level in acute stroke patients. Estimating perfusion parameters accurately and predicting tissue death provides valuable information that may help physicians decide between competing treatment options.

An important advantage of present technology includes a four-dimensional ("4D") CNN architecture that can be used to capture spatial information to model image voxels in three dimensions ("3D"), with a fourth dimension capturing the temporal information of each voxel acquired during perfusion imaging. This enables the deep CNN's to learn 4D spatio-temporal filters (rather than 3D filters) that can extract hierarchical spatio-temporal features, which are more accurate than traditional variables, such as $T_{max}$, in predicting tissue outcome. In addition, the present CNN architecture may be used to learn hidden features that can better estimate the perfusion parameters without need for performing deconvolution analysis used in prior technologies.

Figure 1:
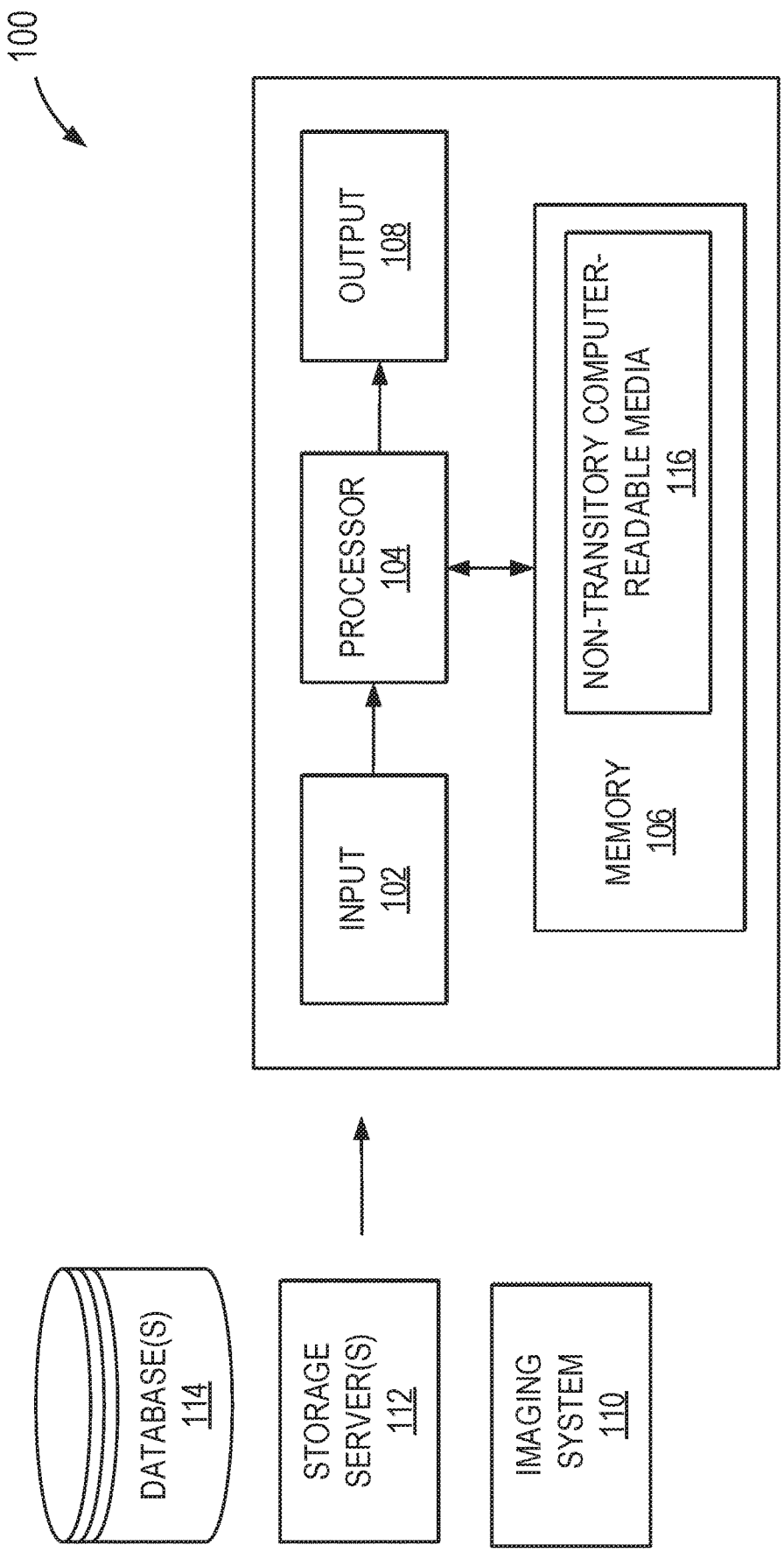
FIG. 1 is a schematic diagram of an example system, in accordance with aspects of the present disclosure.

Turning now to FIG. 1, a block diagram of an example system 100, in accordance with aspects of the present disclosure, is shown. In general, the system 100 may include an input 102, a processor 104, a memory 106, and an output 108, and may be configured to carry out steps analyzing perfusion-weighted imaging in accordance with aspects of the present disclosure.

As shown in FIG. 1, the system 100 may communicate with one or more imaging system 110, storage servers 112, or databases 114, by way of a wired or wireless connection. In general, the system 100 may be any device, apparatus or system configured for carrying out instructions for, and may operate as part of, or in collaboration with various computers, systems, devices, machines, mainframes, networks or servers. In some aspects, the system 100 may be a portable or mobile device, such as a cellular or smartphone, laptop, tablet, and the like. In this regard, the system 100 may be a system that is designed to integrate a variety of software and hardware capabilities and functionalities, and may be capable of operating autonomously. In addition, although shown as separate from the imaging system 110, in some aspects, the system 100, or portions thereof, may be part of, or incorporated into, the imaging system 100, such as the magnetic resonance imaging ("MRI") system described with reference to FIG. 8.

Specifically, the input 102 may include different input elements, such as a mouse, keyboard, touchpad, touch screen, buttons, and the like, for receiving various selections and operational instructions from a user. The input 102 may also include various drives and receptacles, such as flash-drives, USB drives, CD/DVD drives, and other computer-readable medium receptacles, for receiving various data and information. To this end, input 102 may also include various communication ports and modules, such as Ethernet, Bluetooth, or WiFi, for exchanging data and information with these, and other external computers, systems, devices, machines, mainframes, servers or networks.

In addition to being configured to carry out various steps for operating the system 100, the processor 104 may also be programmed to analyze perfusion-weighted imaging according to methods described herein. Specifically, the processor 104 may be configured to execute instructions, stored in a non-transitory computer readable-media 116. Although the non-transitory computer readable-media 116 is shown in FIG. 1 as included in the memory 106, it may be appreciated that instructions executable by the processor 104 may be additionally or alternatively stored in another data storage location having non-transitory computer readable-media.

In some aspects, the processor 104 may be configured to receive and process perfusion-weighted imaging data to generate a variety of information, including perfusion parameters, or parameter maps. By way of example, perfusion-weighted imaging data may include dynamic susceptibility contrast ("DSC") imaging data and dynamic contrast enhanced ("DCE") imaging data, as well as other data. In some aspects, the processor 104 may access information and data, including perfusion-weighted imaging data, stored in the imaging system 110, storage server(s) 112, database(s) 114, PACS, or other data storage location. In other aspects, the processor 104 may direct acquisition of perfusion-weighted and other imaging data, for example, using an MRI system, as described with reference to FIG. 8. The processor 104 may also preprocess the received data and information. For example, the processor 104 may generate one or more images using acquired or received data. In addition, the processor 104 may segment certain portions of the images, such as skull-stripping and ventricles' removal.

Figure 3:
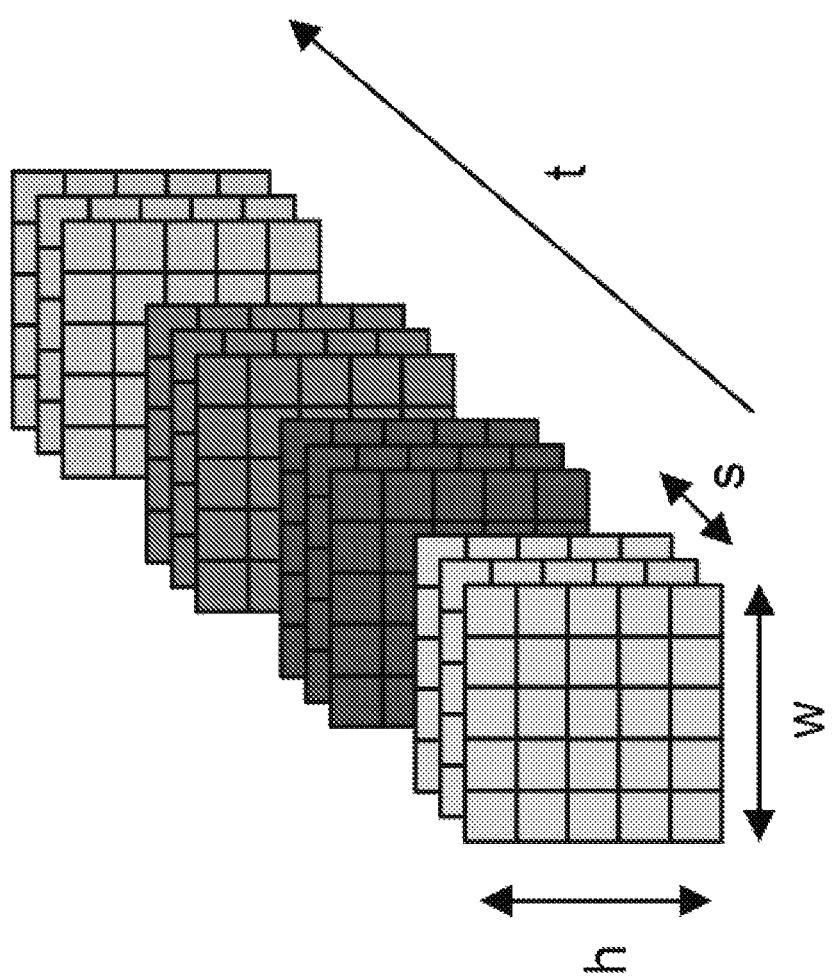
FIG. 3 is an illustration of a four-dimensional ("4D") feature detector, in accordance with aspects of the present disclosure.

In processing perfusion-weighted imaging data, the processor 104 may generate an input patch for each selected voxel and apply a four-dimensional ("4D") convolutional neural network to the generated input patch to extract spatio-temporal features. Each input patch may be defined by a slice number s, a width w, a height h, and a volume number or time t, where the slice number, width and height represent spatial information while the volume number represents temporal information (FIG. 3).

Based on the extracted features, the processor 104 may then compute a variety of information for each selected voxel, including one or more perfusion parameters perfusions. In processing multiple voxels, the processor 104 may generate one or more images or parameter maps. Example perfusion parameters or parameter maps include blood volume ("BV"), blood flow ("BF"), mean transit time ("MTT"), time-to-peak ("TTP"), time-to-maximum ("$T_{max}$"), maximum signal reduction ("MSR"), first moment ("FM"), and others.

As mentioned, the 4D convolutional neural network includes spatial information and temporal information, and may include an input layer, a convolutional layer, a pooling layer, a first fully-connected layer or a non-linear layer, a second fully-connected layer, and an output layer. In some aspects, the 4D convolution neural network may include a non-linear layer inserted between each of the first convolutional layer and the pooling layer. For the output layer, the 4D convolutional neural network may include a classifier layer or non-linear layer connected to the second fully-connected layer. In some aspects, the processor 104 may also be programmed to compute, using the classifier layer, various probabilities based on the spatio-temporal features extracted for selected voxels. The processor 104 may then generate various probability maps using the computed probabilities, including a color-coded map indicating the spatial distribution for the probability of infarction. In other aspects, the processor 104 may be programmed to compute, using the non-linear layer, various perfusion parameters based on the spatio-temporal features extracted for selected voxels.

In some aspects, the processor 104 may be configured to identify various imaged tissues based on computed perfusion parameters. For example, the processor 104 may identify infarct core and penumbra regions, as well as regions associated with abnormal perfusion. The processor 104 may be further programmed to determine a condition of the subject. For example, based on identified tissues or tissue regions, the processor 104 may determine a risk to the subject, such as a risk of infarction.

The processor 104 may also be configured to generate a report, in any form, and provide it via output 108. In some aspects, the report may include various raw or processed maps or images, or color-coded maps or images. For example, the report may include anatomical images, maps of CBF, CBV, MTT, TPP, $T_{max}$ and other perfusion parameters as well as probability maps. In some aspects, the report may indicate specific regions or tissues of interest, as well as other information. The report may further indicate a condition of the subject or a risk of the subject to developing an acute or chronic condition, such as a risk of infarction.

Embodiments of the present technology may be described with reference to flowchart illustrations of methods and systems according to embodiments of the technology, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a system 100 as described with reference to FIG. 1, as well as any other computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory in the form of non-transitory computer-readable media, that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

It will further be appreciated that the terms "programming" or "program executable" as used herein refer to one or more instructions that can be executed by a processor to perform a function as described herein. The instructions can be embodied in software, in firmware, or in a combination of software and firmware. The instructions can be stored local to the device in non-transitory media, or can be stored remotely such as on a server, or all or a portion of the instructions can be stored locally and remotely. Instructions stored remotely can be downloaded (pushed) to the device by user initiation, or automatically based on one or more factors. It will further be appreciated that as used herein, that the terms processor, computer processor, central processing unit ("CPU"), and computer are used synonymously to denote a device capable of executing the instructions and communicating with input/output interfaces and/or peripheral devices.

Figure 2:
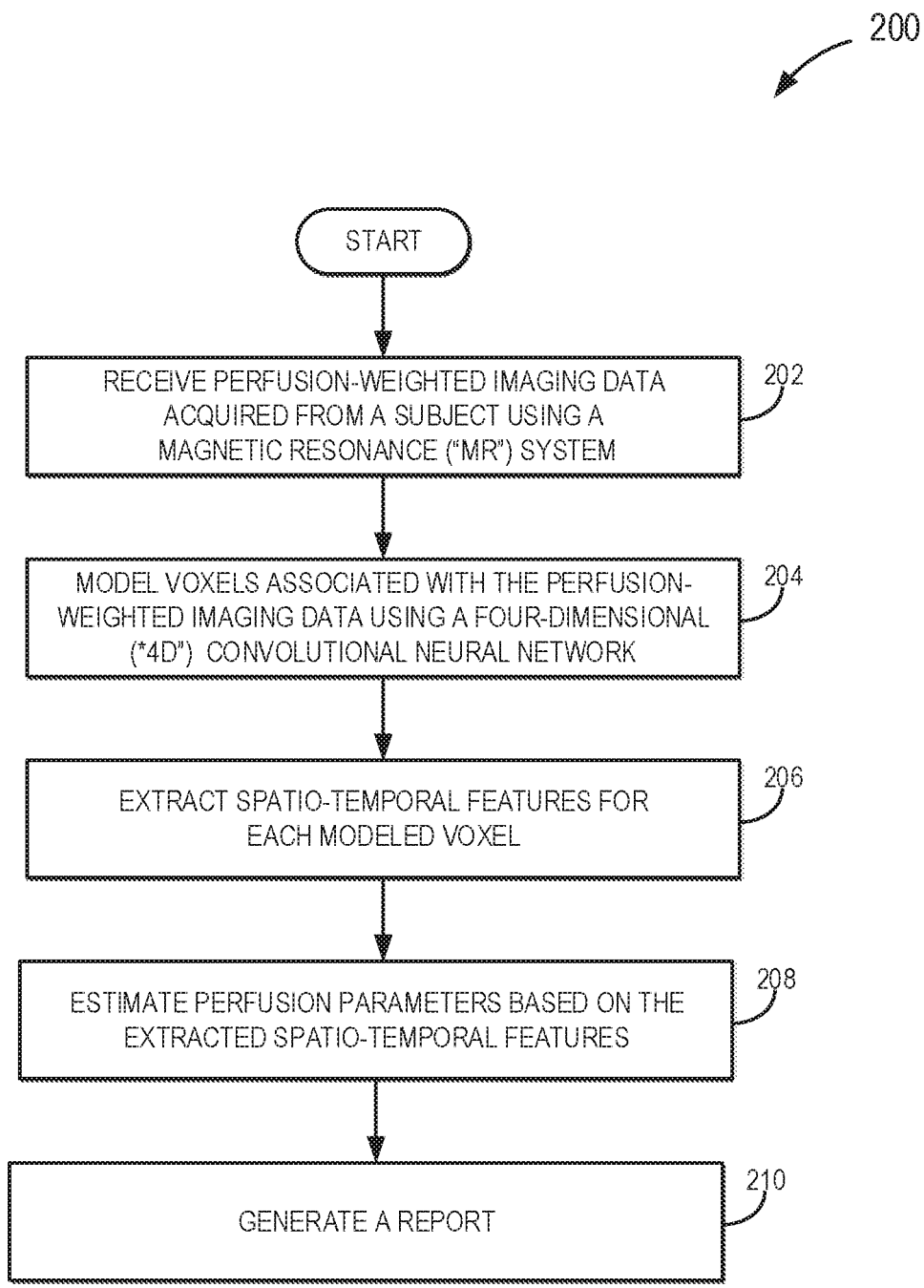
FIG. 2 is a flowchart setting forth steps of a process, in accordance with aspects of the present disclosure.

Turning now to FIG. 2, a flowchart setting forth steps of a process 200, in accordance with aspects of the present disclosure is shown. The process 200 may be carried out using any suitable system, device or apparatus, such as the system 100 described with reference to FIG. 1. In some aspects, the process 200 may be embodied in a program or software in the form of instructions, executable by a computer or processor, and stored in non-transitory computer-readable media.

The process 200 may begin at process block 202 with receiving perfusion-weighted imaging data. Generally speaking, the perfusion-weighted imaging data may be acquired using an MRI system, as described with reference to FIG. 8, although similar acquisitions may be possible with a CT system using different contrast agents and techniques. For instance, the perfusion-weighted imaging data may be obtained using a perfusion acquisition such as dynamic susceptibility contrast ("DSC") images or dynamic contrast enhanced ("DCE") images that are obtained during the administration of an intravascular contrast agent to the subject, or perfusion images gathered without the use of contrast agents, such as arterial spin labeling ("ASL"). The perfusion-weighted imaging data may be obtained as a time-resolved series of images, in which each image in the series depicts an imaged object or subject at a different time point. Anatomical images may also be received in addition to the perfusion-weighted images. As described perfusion-weighted and other imaging data may be accessed from a memory, database, or other data storage location.

At process block 204, various selected voxels associated with the received perfusion-weighted imaging data may be modeled using a 4D convolutional neural network. In the model, one or more an input patches may be generated for each selected voxel. Particularly, each input patch may be defined by a slice number s, a width w, a height h, and a volume number or time t, where the slice number, width and height represent spatial information while the volume number represents temporal information. In applying the 4D convolutional neural network to the generated input patches, one or more spatio-temporal may be extracted, as indicated by process block 206.

By way of example, the 4D convolution neural network may include a deep CNN architecture based on multiple layers, categorized into four types: convolutional, pooling, non-linear, and fully-connected. In the convolutional layer, each of the output neurons may be only connected to a local volume (e.g., 3 slices×5 pixels×5 pixels×40 time channels) of the input neurons via a weight vector, which is called feature filter (detector). Instead of common 3D feature filters (#color channel×width× height) included in typical CNNs, the convolutional layer described herein is extended to multiple 4D feature filters (#slices× width× height×#time channels) to be learned. Through learning these 4D feature detectors (FIG. 3), elementary features such as oriented edges, endpoints, and corners may be extracted along time from the input patches, and thus capturing both regional and temporal features. Each convolutional layer can learn multiple 4D feature filters that capture hierarchical features from the previous input layer and generate useful feature maps that will be used as input for the next layer. In the pooling layer, local groups of input values are "pooled" together via a max-operator to not only reduce the size of inputs, but also produce outputs (representations) that are robust to local transformations (i.e. translation invariance).

In some aspects, a non-linear layer may be inserted between each of the convolutional layer and pooling layer to introduce non-linearity to the network. Activation functions may be used to bound neuron output. By way of example, Rectified Linear Unit ("ReLU") has been found to obtain convergence in a faster manner compared to traditional activation functions, although other functions may be possible. The fully-connected layer may include output neurons that are fully connected to input neurons (i.e. each output neuron is connected to all the input neurons). In some aspects, a deep CNN architecture may include multiple sequences of convolutional-ReLU-pooling layers, followed by several fully-connected layers. The last fully-connected layer can include rich representations that characterize a voxel input signal and these features can be used for a variety of tasks, including: 1) in a softmax classifier to predict tissue death, for example; 2) in a non-linear unit to estimate a perfusion parameter, for example. The weights on the 4D convolution neural network may be learned from batch stochastic gradient descent via backpropagation. The hyperparameters of the network (the number of filters in each convolutional layer, the size of the filters, the depth of the network, and the learning rate) can be further optimized via five-fold cross-validation using random search.

Referring again to FIG. 2, at process block 208, one or more perfusion parameters may then be estimated based on the extracted spatio-temporal features. In some aspects, the estimated perfusion parameters may be used to generate at least one image or map. Example maps include blood volume ("BV"), blood flow ("BF"), mean transit time ("MTT"), time-to-peak ("TTP"), time-to-maximum ("$T_{max}$"), maximum signal reduction ("MSR"), first moment ("FM") and other maps. In some aspects, various probabilities may be computed at process block 208 based on the spatio-temporal features extracted for selected voxels, using a classifier layer in the 4D convolution neural network. By way of example, probabilities of infarction may be computed. As such, various probability maps may be generated using the computed probabilities.

A report may then be generated at process block 210. The report may be in any form, and provide various information. In some aspects, the report may include various raw or processed maps or images, or color-coded maps or images. For example, the report may include anatomical images, maps of CBF, CBV, MTT, TPP, $T_{max}$ and other perfusion parameters as well as probability maps. In some aspects, the report may indicate or highlight specific regions or tissues of interest, as well as provide other information. The report may further indicate a condition of the subject or a risk of the subject to developing an acute or chronic condition, such as a risk of infarction. To this end, generated perfusion parameters, probabilities, maps or images may be analyzed to determine the condition or tissue types, or tissue regions.

Figure 4:
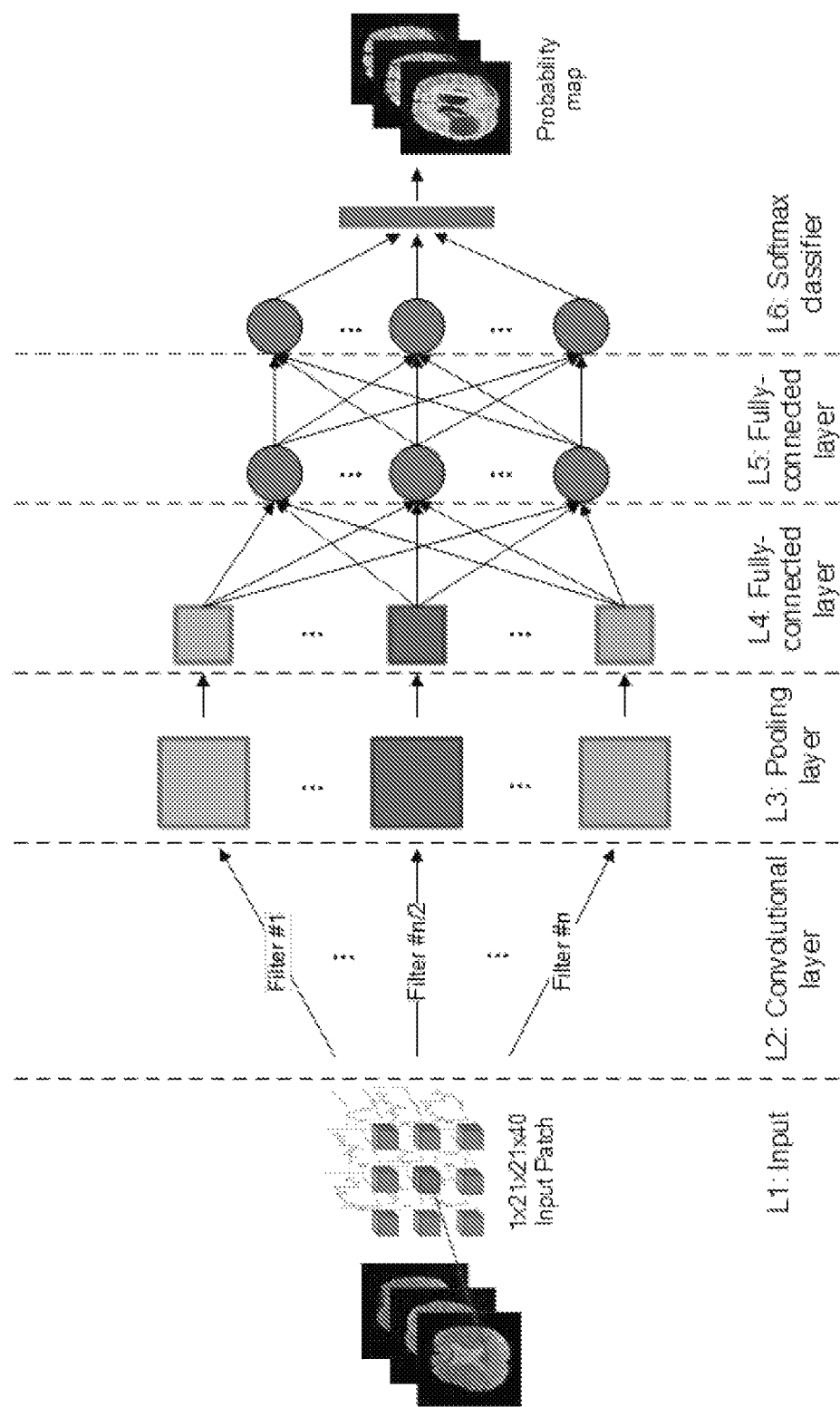
FIG. 4 is an illustration showing a 4D convolutional neural network architecture, in accordance with aspects of the present disclosure.

By way of example, FIG. 4 illustrates the steps of a process for using CNN, in accordance with the present disclosure, to produce a probability map for infarct prediction: 1) provide a patient's PWIs. For example, pre-treatment PWIs (pre-processed with skull-stripping and ventricles' removal) and PWIs acquired 3-to-7 days post-treatment using fluid-attenuated inversion recovery ("FLAIR") sequences may be provided; 2) for a voxel in the first volume of pre-treatment PWIs, the neighboring voxels (3D volume) are selected and used to generate an input patch with a dimension of s×w×h, where the center of the input patch is the voxel of interest and the dimensions s, w, h may depend on the filters' size of the first or input layer (L1). Temporal information may then be included by adding another dimension to the input patch, namely t, which represents time or volumes in acquired PWIs, to produce an input patch defined by s×w×h×t; As shown in FIG. 4, as a non-limiting example, an input patch may be 1×21×21×40, although other dimensions may be possible; 3) the CNN consisting of a convolutional layer (L2), a pooling layer (L3), a first fully connected layer (L4) and a second fully connected layer (L5) may then be applied to the input patch and features may generated in the second fully-connected layer (L5); For the output layer (L6), a softmax classifier layer may be used to calculate the probability of infarction based on the features; Steps 1 and 2 may be repeated by feeding each input patch into the network, until all desired voxels are analyzed, thereby producing a number of probabilities, that can be assembled to produce one or more infarction probability maps, as shown in FIG. 4. In some alternatives, the above steps may be repeated to produce perfusion parameters, and one or more perfusion maps therefrom (e.g., $T_{max}$ maps). To this end, a non-linear layer may be used instead of the softmax classifier layer in the output layer (L6).

Figure 5A:
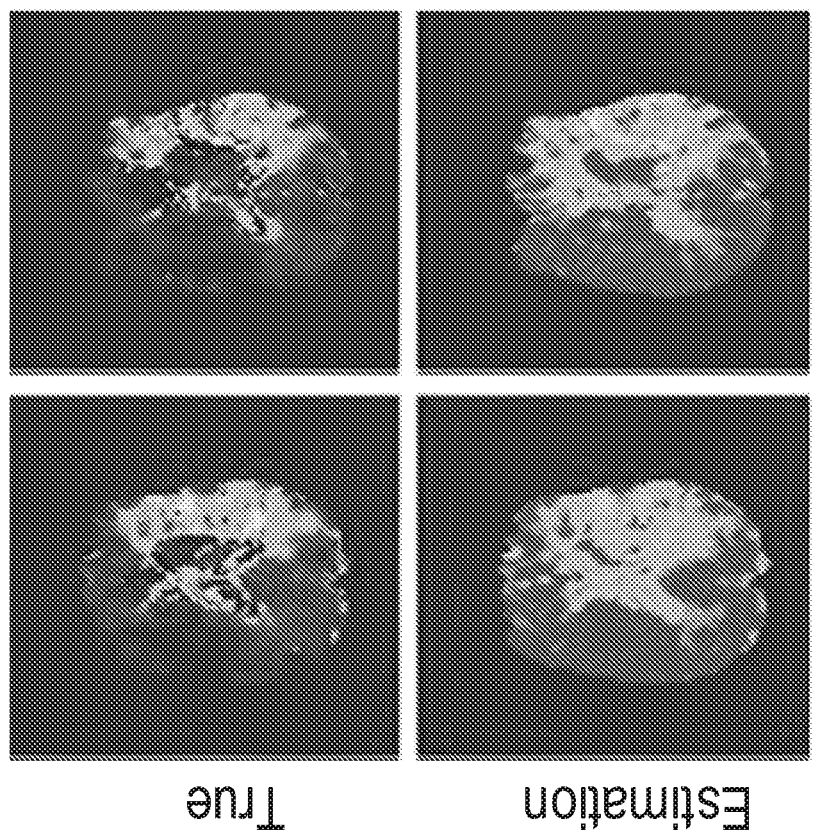
FIG. 5A shows a comparison between a FLAIR image (top) and a probability of infarction map (bottom), generated in accordance with aspects of the present disclosure.
Figure 5B:
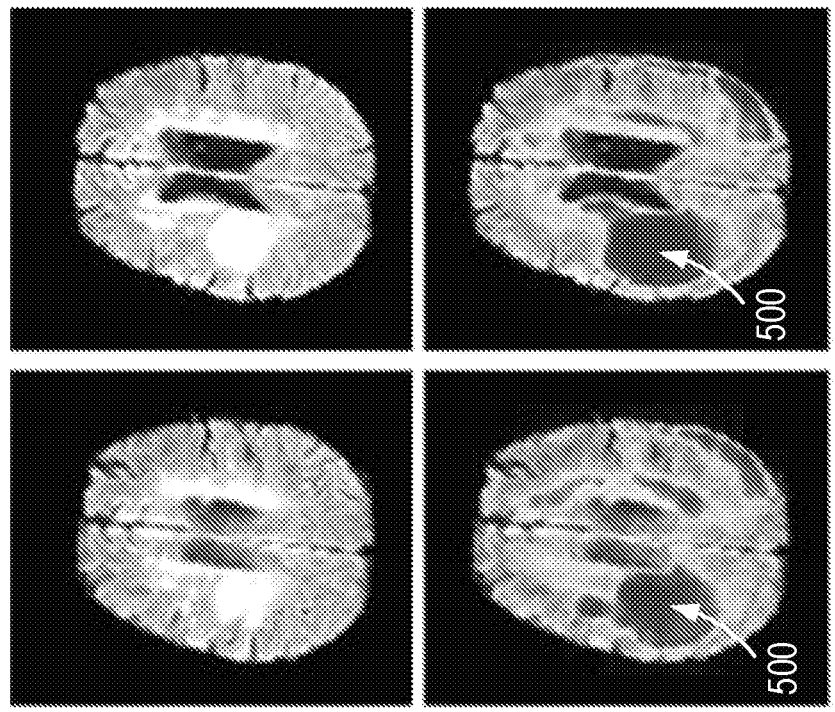
FIG. 5B shows a comparison between a labeled perfusion map (top) and a perfusion map (bottom) estimated in accordance with the present disclosure.
Figure 6:
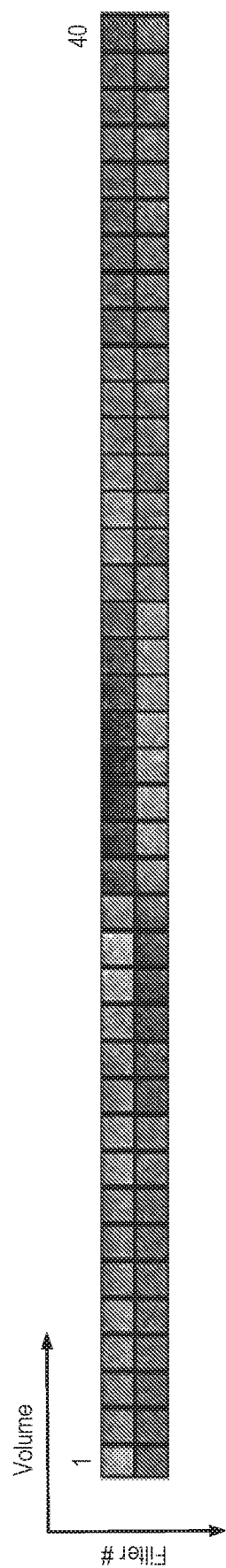
FIG. 6 shows example spatio-temporal filters learned in accordance with aspects of the present disclosure.

In demonstrating the present approach, two deep CNNs were built in accordance with the present disclosure to perform infarction prediction and $T_{max}$ estimation, with results shown in FIG. 5A-5B. FIG. 5A shows a probability map (bottom) generated in accordance with the present disclosure in comparison to a post-treatment FLAIR image (top). Regions 500 with a high probability of infarction (dark red) are mostly aligned with true infarcted tissue as measured on the FLAIR image acquired 3-7 days after treatment, illustrating that the deep CNN approach is able to correctly predict infarctions. FIG. 5B shows a $T_{max}$ perfusion map (bottom) estimated in accordance with the present disclosure in comparison to a labeled perfusion map (top). It may be observed that the estimated perfusion map is mostly aligned with the labeled perfusion map, showing effectiveness of the method. In additional, the results show that the present deep CNN is capable of learning spatio-temporal filters for PWIs. As an illustration, FIG. 6 shows two example spatio-temporal filters from pre-treatment PWIs. Each row corresponds to one filter, and each column corresponds to a 2D filter at a particular volume (time) in pre-treatment PWIs. The spatial changes of the intensity along volumes (times) of a filter demonstrate the ability of the present approach to extract spatial and temporal information from the inputs. As such, these powerful filters extract hierarchical features can be useful for the prediction of infarcts.

Figure 7:
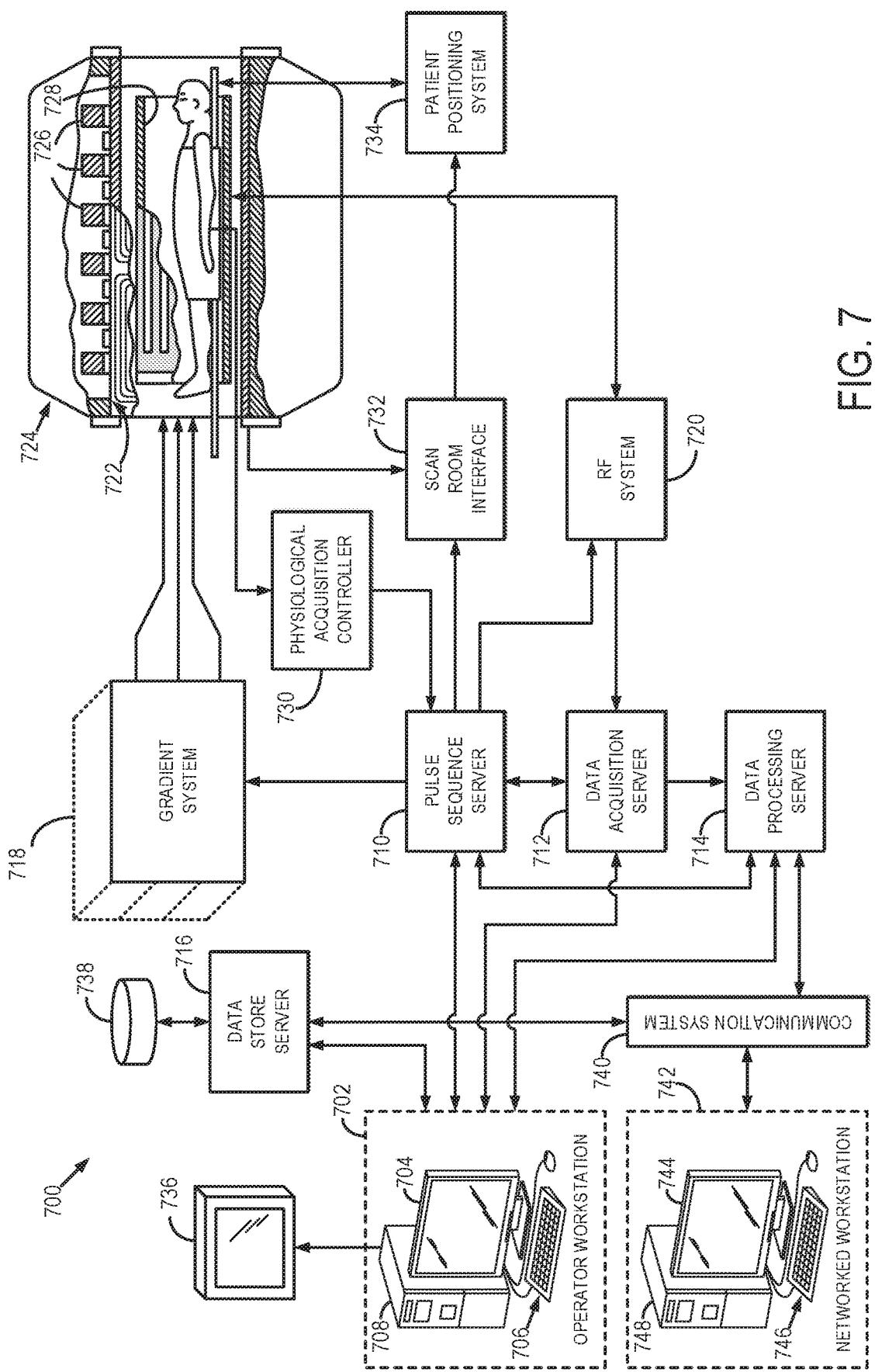
FIG. 7 is a block diagram of an example magnetic resonance imaging ("MRI") system, in accordance with aspects of the present disclosure.

Referring particularly now to FIG. 7, an example of a magnetic resonance imaging ("MRI") system 700 that may be used to implement the systems and methods of the present disclosure is illustrated. The MRI system 700 includes a workstation 702 having a display 704 and a keyboard 706. The workstation 702 includes a processor 708, such as a commercially available programmable machine running a commercially available operating system. The workstation 702 provides the operator interface that enables scan prescriptions to be entered into the MRI system 700. The workstation 702 is coupled to servers, including a pulse sequence server 710, a data acquisition server 712, a data processing server 714, and a data store server 716. The workstation 702 and each server 710, 712, 714, and 716 are in communication.

The pulse sequence server 710 functions in response to instructions downloaded from the workstation 702 to operate a gradient system 718 and a radiofrequency ("RF") system 720. Gradient waveforms necessary to perform the prescribed scan are produced and applied to the gradient system 718, which excites gradient coils in an assembly 722 to produce the magnetic field gradients $G_x$, $G_y$, and $G_z$ used for position encoding MR signals. The gradient coil assembly 722 forms part of a magnet assembly 724 that includes a polarizing magnet 726 and a whole-body RF coil 728.

RF excitation waveforms are applied to the RF coil 728, or a separate local coil (not shown in FIG. 7), by the RF system 720 to perform the prescribed magnetic resonance pulse sequence. Responsive MR signals detected by the RF coil 728, or a separate local coil, are received by the RF system 720, amplified, demodulated, filtered, and digitized under direction of commands produced by the pulse sequence server 710. The RF system 720 includes an RF transmitter for producing a wide variety of RF pulses used in MR pulse sequences. The RF transmitter is responsive to the scan prescription and direction from the pulse sequence server 710 to produce RF pulses of the desired frequency, phase, and pulse amplitude waveform. The generated RF pulses may be applied to the whole body RF coil 728 or to one or more local coils or coil arrays.

The RF system 720 also includes one or more RF receiver channels. Each RF receiver channel includes an RF preamplifier that amplifies the MR signal received by the coil 728 to which it is connected, and a detector that detects and digitizes the I and Q quadrature components of the received MR signal. The magnitude of the received MR signal may thus be determined at any sampled point by the square root of the sum of the squares of the I and Q components:

$$M=\sqrt{I^2+Q^2} \qquad (1);$$

and the phase of the received MR signal may also be determined:

$$\varphi = \tan^{-1}\left(\frac{Q}{I}\right). \qquad (2)$$

The pulse sequence server 710 also optionally receives patient data from a physiological acquisition controller 730. The controller 730 receives signals from a number of different sensors connected to the patient, such as electrocardiograph ("ECG") signals from electrodes, or respiratory signals from a bellows or other respiratory monitoring device. Such signals are typically used by the pulse sequence server 710 to synchronize, or "gate," the performance of the scan with the subject's heart beat or respiration.

The pulse sequence server 710 also connects to a scan room interface circuit 732 that receives signals from various sensors associated with the condition of the patient and the magnet system. It is also through the scan room interface circuit 732 that a patient positioning system 734 receives commands to move the patient to desired positions during the scan.

The digitized MR signal samples produced by the RF system 720 are received by the data acquisition server 712. The data acquisition server 712 operates in response to instructions downloaded from the workstation 702 to receive the real-time MR data and provide buffer storage, such that no data is lost by data overrun. In some scans, the data acquisition server 712 does little more than pass the acquired MR data to the data processor server 714. However, in scans that require information derived from acquired MR data to control the further performance of the scan, the data acquisition server 712 is programmed to produce such information and convey it to the pulse sequence server 710. For example, during prescans, MR data is acquired and used to calibrate the pulse sequence performed by the pulse sequence server 710. Also, navigator signals may be acquired during a scan and used to adjust the operating parameters of the RF system 720 or the gradient system 718, or to control the view order in which k-space is sampled. In all these examples, the data acquisition server 712 acquires MR data and processes it in real-time to produce information that is used to control the scan.

The data processing server 714 receives MR data from the data acquisition server 712 and processes it in accordance with instructions downloaded from the workstation 702. Such processing may include, for example: Fourier transformation of raw k-space MR data to produce two or three-dimensional images; the application of filters to a reconstructed image; the performance of a backprojection image reconstruction of acquired MR data; the generation of functional MR images; and the calculation of motion or flow images.

Images reconstructed by the data processing server 714 are conveyed back to the workstation 702 where they are stored. Real-time images are stored in a data base memory cache, from which they may be output to operator display 712 or a display 736 that is located near the magnet assembly 724 for use by attending physicians. Batch mode images or selected real time images are stored in a host database on disc storage 738. When such images have been reconstructed and transferred to storage, the data processing server 714 notifies the data store server 716 on the workstation 702.

The MRI system 700 may also include one or more networked workstations 742. By way of example, a networked workstation 742 may include a display 744, one or more input devices 746 (such as a keyboard and mouse or the like), and a processor 748. The networked workstation 742 may be located within the same facility as the operator workstation 702, or in a different facility, such as a different healthcare institution or clinic. The networked workstation 742 may include a mobile device, including phones or tablets.

The networked workstation 742, whether within the same facility or in a different facility as the operator workstation 702, may gain remote access to the data processing server 714 or data store server 716 via the communication system 740. Accordingly, multiple networked workstations 742 may have access to the data processing server 714 and the data store server 716. In this manner, magnetic resonance data, reconstructed images, or other data may exchanged between the data processing server 714 or the data store server 716 and the networked workstations 742, such that the data or images may be remotely processed by a networked workstation 742. This data may be exchanged in any suitable format, such as in accordance with the transmission control protocol ("TCP"), the internet protocol ("IP"), or other known or suitable protocols.

The present invention has been described in terms of one or more preferred embodiments, and it should be appreciated that many equivalents, alternatives, variations, and modifications, aside from those expressly stated, are possible and within the scope of the invention.

The invention claimed is:

1. A computer-implemented method for analyzing perfusion-weighted imaging, the method comprising:
   a) receiving perfusion-weighted imaging data acquired from a subject having received an injection of a contrast agent using a magnetic resonance ("MR") imaging system;
   b) modeling at least one voxel associated with the perfusion-weighted imaging data using a four-dimensional ("4D") convolutional neural network;
   c) extracting spatio-temporal features for each modeled voxel;
   d) estimating at least one perfusion parameter for each modeled voxel based on the extracted spatio-temporal features; and e) generating a report using the at least one perfusion parameter indicating perfusion in the subject.

2. The method of claim 1, wherein the perfusion-weighted imaging data comprises at least one of dynamic susceptibility contrast ("DSC") imaging data and dynamic contrast enhanced ("DCE") imaging data.

3. The method of claim 1, wherein the 4D convolutional neural network comprises spatial information and temporal information.

4. The method of claim 1, wherein the 4D convolution neural network comprises at least one of a convolutional, a pooling, a non-linear, and a fully-connected layer.

5. The method of claim 4, wherein the 4D convolution neural network further comprises a non-linear layer inserted between each of the convolutional layer and the pooling layer.

6. The method of claim 1, wherein the method further comprises generating at least one input patch defined by a slice number, a width, a height, and a volume number for each modeled voxel.

7. The method of claim 6, wherein the method further comprises providing the at least one input patch to the 4D convolutional neural network to extract the spatio-temporal features.

8. The method of claim 1, wherein the method further comprises computing, using a classifier layer in the 4D convolution neural network, at least one probability of infarction based on the spatio-temporal features extracted.

9. The method of claim 8, wherein the method further comprises generating a probability map using the at least one probability computed.

10. The method of claim 1, wherein the method further comprises determining a condition of the subject based on the at least one perfusion parameter.

11. The method of claim 1, wherein the at least one perfusion parameter comprises at least one of a blood volume ("BV"), a blood flow ("BF"), a mean transit time ("MTT"), a time-to-peak ("TTP"), a time-to-maximum ("$T_{max}$"), a maximum signal reduction ("MSR"), and a first moment ("FM").

12. A system for analyzing perfusion-weighted imaging, the system comprising:
  an input configured to receive perfusion-weighted imaging data acquired from a subject using a magnetic resonance ("MR") imaging system;
  a processor programmed execute instructions stored in a non-transitory computer readable media to:
    i) access the perfusion-weighted imaging data;
    ii) generate an input patch for each selected voxel associated with the perfusion-weighed imaging data;
    iii) apply a four-dimensional ("4D") convolutional neural network to the generated input patch to extract spatio-temporal features;
    iv) compute, at least one perfusion parameter using the spatio-temporal features extracted;
    v) generate a report using the at least one perfusion parameter; and
  an output for displaying the report to communicate perfusion in the subject.

13. The system of claim 12, wherein the perfusion-weighted imaging data comprises at least one of dynamic susceptibility contrast ("DSC") imaging data and dynamic contrast enhanced ("DCE") imaging data.

14. The system of claim 12, wherein the 4D convolutional neural network comprises spatial information and temporal information.

15. The system of claim 12, wherein the 4D convolution neural network comprises at least one of a convolutional, a pooling, a non-linear, and a fully-connected layer.

16. The system of claim 15, wherein the 4D convolution neural network further comprises a non-linear layer is inserted between each of the convolutional layer and the pooling layer.

17. The system of claim 12, wherein the processor is further programmed to compute, using a classifier layer in the 4D convolution neural network, at least one probability of infarction based on the spatio-temporal features extracted.

18. The system of claim 17, wherein the processor is further programmed to generate a probability map using the at least one probability computed for each of plurality of selected voxels.

19. The system of claim 12, wherein the at least one perfusion parameter comprises at least one of a blood volume ("BV"), a blood flow ("BF"), a mean transit time ("MTT"), a time-to-peak ("TTP"), a time-to-maximum ("$T_{max}$"), a maximum signal reduction ("MSR"), and a first moment ("FM").

20. The system of claim 12, wherein the processor is further programmed to generate at least one image by the at least one perfusion parameter computed for each of a plurality of selected voxels.

21. The system of claim 11, wherein the processor is further programmed to determine a condition of the subject based on the at least one perfusion parameter.

22. The method of claim 1, wherein the 4D convolutional neural network is configured to capture spatial for each modeled voxel in three dimensions ("3D") and capture temporal information of each modeled voxel in a fourth dimension of the 4D convolutional neural network.

23. The system of claim 12, wherein the 4D convolutional neural network is configured to capture spatial for each modeled voxel in three dimensions ("3D") and capture temporal information of each modeled voxel in a fourth dimension of the 4D convolutional neural network.

* * * * *